United States Patent
Fujitsu et al.

[11] Patent Number: 5,686,109
[45] Date of Patent: Nov. 11, 1997

[54] ANTIPYRETIC ANALGESIC COMPOSITION

[75] Inventors: Takashi Fujitsu, Osaka; Kikuko Yoneda, Matsuomura; Isao Ikebe, Yamatokooriyama, all of Japan

[73] Assignee: Fujisawa Pharmaceutical Co., Ltd., Osaka, Japan

[21] Appl. No.: 647,898

[22] PCT Filed: Dec. 2, 1994

[86] PCT No.: PCT/JP94/02031

§ 371 Date: Jul. 25, 1996

§ 102(e) Date: Jul. 25, 1996

[87] PCT Pub. No.: WO95/15751

PCT Pub. Date: Jun. 15, 1995

[30] Foreign Application Priority Data

Dec. 10, 1993 [JP] Japan ..................... 5-310803
Apr. 14, 1994 [JP] Japan ..................... 6-075638

[51] Int. Cl.$^6$ ........................ A61K 9/24
[52] U.S. Cl. ........... 424/464; 424/472; 424/480
[58] Field of Search ..................... 424/472, 480, 424/464; 514/568; 562/496

[56] References Cited

U.S. PATENT DOCUMENTS

| | | | |
|---|---|---|---|
| 4,310,521 | 1/1982 | Aonuma | 424/232 |
| 4,702,918 | 10/1987 | Ushimaru et al. | 424/461 |
| 4,831,058 | 5/1989 | Phankhania et al. | 514/570 |
| 5,213,807 | 5/1993 | Chemburkar et al. | 424/472 |
| 5,368,861 | 11/1994 | Ushimaru et al. | 424/451 |
| 5,431,916 | 7/1995 | White | 424/455 |
| 5,498,422 | 3/1996 | Nakamichi et al. | 424/451 |

*Primary Examiner*—Thurman K. Page
*Assistant Examiner*—Murthy Sikha
*Attorney, Agent, or Firm*—Oblon, Spivak, McClelland, Maier & Neustadt, P.C.

[57] ABSTRACT

This invention provides an antipyretic analgesic preparation having good antipyretic and analgesic effects with reduced adverse effects such as gastrointestinal disorders. The object is achieved by providing a mixture composition containing ibuprofen and isopropylantipyrine. The ratio between them is preferably 5:1 to 1:5, more preferably 3:1 to 1:3, on the weight basis. Preferred dosage forms of the mixture composition are a three-layer tablet comprising an ibuprofen-containing first layer, an isopropylantipyrine-containing third layer, and a second layer composed of one or more inactive ingredients alone as provided between said first and third layers, a dry coated tablet internally having an ibuprofen- or isopropylantipyrine-containing core tablet, and so forth.

10 Claims, No Drawings

ANTIPYRETIC ANALGESIC COMPOSITION

This application is an 35USC 31L of PCT/JP94/0231 filed Dec. 2, 1994.

TECHNICAL FIELD

This invention relates to an antipyretic analgesic composition containing ibuprofen and isopropylantipyrine and producing excellent antipyretic and analgesic effects and, more particularly, to three-layer tablets and dry coated tablets, which are utilized in the field of medicine.

BACKGROUND ART

Ibuprofen (2-(4-isobutylphenyl)propionic acid) is a nonsteroid antiinflammatory agent and has excellent antiinflammatory, analgesic and antipyretic activities. It is widely used also in the form of over-the-counter drugs containing it alone or in combination with one or more other active ingredients.

On the other hand, isopropylantipyrine (4-isopropyl-2,3-dimethyl-1-phenyl-3-pyrazolin-5-one) is an antipyretic analgesic of the pyrazolone type. It is used not only as such but also in combination with one or more other analgesic, antipyretic and/or antiinflammatory agents, such as phenacetin, bromodiethylacetylurea, butylisopropylurea, ephedrine, acetaminophen, ethenzamide, caffeine, etc.

However, no mixture composition comprising ibuprofen and isopropylantipyrine is known.

For developing an antipyretic analgesic agent as a drug, in particular as an over-the-counter drug which is freely available for consumers, a preparation is required with which the manifestation of adverse effects is slight and satisfactory antipyretic and analgesic effects can be obtained.

However, ibuprofen causes such adverse effects as gastrointestinal disorders, for example nausea, vomiting, anorexia, pyrosis and the like.

Isopropylantipyrine also has its drawback in that it causes similar gastrointestinal disorders although such disorders are less in degree as compared with ibuprofen.

DISCLOSURE OF THE INVENTION

As a result of intensive investigations made by the present inventors in an attempt to solve the problem mentioned above, it has now been found that when ibuprofen (hereinafter sometimes referred to as "IBP") and isopropylantipyrine (hereinafter sometimes referred to as "IPA") are used combinedly, markedly increased antipyretic and analgesic effects are produced as compared with the cases where IBP and IPA are used each alone separately, with the result that gastrointestinal disorders and other adverse effects can be mitigated.

The proportion of ibuprofen to isopropylantipyrine in the mixture composition of this invention is preferably in the range of 5:1 to 1:5, more preferably in the range of 3:1 to 1:3, on the weight basis.

Preferred examples of said proportion, on the weight basis, of IBP to IPA are thus 5:1, 4:1, 3:1, 2:1, 3:2, 1:1, 2:3, 1:2, 1:3, 1:4, 1:5, and so on.

For use as an over-the-counter drug in Japan, for instance, the mixture composition of this invention contains IBP and IPA in such a proportion as mentioned above, with the maximum daily dose of either of them being taken as 450 mg.

The mixture composition of this invention can be prepared by admixing one or more of the additives mentioned below, each in an appropriate amount, with ibuprofen and isopropylantipyrine. It can then be made up into any of the dosage forms suited for oral administration, for example tablets, hard capsules, soft capsules, powders, granules, fine granules, solutions, syrups and the like, by a per se known method, for example by one of the methods described in the 12th edition of Japanese Pharmacopeia, General rules for preparations.

The additives to be used in dosage form production includes, for example, excipients (e.g. lactose, corn starch, light anhydrous silicic acid, microcrystalline cellulose, etc.), binders (e.g. methylcellulose, carboxymethylcellulose, hydroxypropylcellulose, hydroxypropylmethylcellulose, polyvinylpyrrolidone, etc.), disintegrators (e.g. carboxymethylcellulose calcium, carboxymethylcellulose sodium, low substituted hydroxypropylcellulose, etc.), lubricants (e.g. magnesium stearate, talc, etc.), sweetening agents (e.g. sucrose, D-sorbitol, saccharin sodium, etc.), preservatives (e.g. sodium benzoate, parabens, etc.), thickening agents (e.g. methylcellulose etc.), and the like.

In the case of tablets, granules or fine granules, they may be coated by a per se known method for the purpose of taste masking, stability maintenance and/or the like. The coating agent to be used for that purpose is, for example, hydroxypropylmethylcellulose, hydroxymethylcellulose, hydroxypropylcellulose, polyoxyethylene glycol or the like. Where appropriate, a coloring matter such as talc, titanium oxide or yellow iron sesquioxide and/or other additives may be added thereto.

In producing conventional tablets containing ibuprofen and isopropylantipyrine combinedly, contacting between both ingredients results in melting point depression and, as a result, the frictional heat generated during kneading, blending and granule size adjustment causes melting of the ingredients. The heat in the step of drying also causes such melting.

Furthermore, the frictional heat generated in the step of tableting causes material adhesion to the turntable of the tableting machine, disturbing the production process.

In addition, it is a problem that even during storage, the tablets, if exposed to a temperature exceeding 40° C. lose shape as a result of said melting.

Conventionally, these problems are solved by using an adsorbent excipient in large amounts. However, this increases the tablet size, making it difficult to take the tablets.

The inventors of this invention made intensive investigations to solve the above problems and, as a result, succeeded in solving the above-mentioned process disturbance and elevated temperature storage stability problems by avoiding contacting of ibuprofen with isopropylantipyrine by producing three-layer tablets comprising an ibuprofen-containing first layer, an isopropylantipyrine-containing third layer and a second layer composed of one or more inactive ingredients as provided between the first and third layers, or by producing dry coated tablets internally having an ibuprofen- or isopropylantipyrine-containing core tablet. Furthermore, the inventors succeeded in producing three-layer tablets and dry coated tablets which need an excipient and so forth only in reduced amounts and are easy to take.

Surprisingly, it was further found that an increased Cmax (maximum plasma concentration) and increased bioavailability of ibuprofen can be attained with said three-layer tablets as compared with the conventional tablets.

The three-layer tablets of this invention are characterized in that a second layer composed of one or more inactive ingredients alone is provided between an ibuprofen-containing first layer and an isopropylantipyrine-containing third layer.

The three-layer tablets of this invention are produced in the following manner.

First, an excipient (e.g. lactose, corn starch, light anhydrous silicic acid, microcrystalline cellulose, etc.), a binder (e.g. methylcellulose, carmellose, hydroxypropylcellulose, hydroxypropylmethylcellulose, polyvinylpyrrolidone, etc.), a disintegrator (e.g. carmellose calcium, crosscarmellose sodium, carmellose, low substituted hydroxypropylcellulose, etc.) and so forth are added to and mixed with ibuprofen and, after addition of purified water and of ethanol as necessary, the mixture is kneaded and then granulated in the conventional manner using a granulator, cylindrical granulator, sieve or the like, followed by drying and granule size adjustment, to give granules.

In producing such ibuprofen-containing granules, such an ingredient as anhydrous caffeine, bromovalerylurea, allylisopropylacetylurea, bromodiethylacetylurea, butylisopropylurea or ephedrine, may further be incorporated.

Then, a lubricant (e.g. magnesium stearate, talc, etc.) and, when desired, a small amount of the excipient, binder and/or disintegrator mentioned above, are added to and mixed with said granules to give ibuprofen-containing granules for tableting.

Separately, isopropylantipyrine-containing granules for tableting are produced in the same manner as in the ibuprofen-containing tableting granules.

Further, granules for tableting which are composed of inactive ingredients alone are produced by mixing up the above-mentioned excipient, binder, disintegrator, lubricant and so forth.

The term "inactive ingredient" as used herein means any ingredient other than ibuprofen and isopropylantipyrine and thus includes not only mere excipients, binders, disintegrators, lubricants and the like but also pharmacologically active ingredients such as those mentioned above, namely anhydrous caffeine, bromovalerylurea, allylisopropylacetylurea, bromodiethylacetylurea, butylisopropylurea, ephedrine, etc.

Thus, anhydrous caffeine, for example, may be added to the above-mentioned granules for tableting.

Three-layer tablet production is carried out by placing the ibuprofen-containing tableting granules produced in the above manner in a die of the tableting machine, lightly precompressing them, shifting the die to the next place on the turntable, placing on the precompressed granules the inactive ingredient granules for tableting, lightly precompressing them, further shifting the mortar to the next place on the turntable, placing the isopropylantipyrine-containing tableting granules on the precompressed two-layer mass and subjecting the whole mortar contents to compression proper.

In this manner, three-layer tablets having a second layer of inactive ingredients as formed between an ibuprofen-containing first layer and an isopropylantipyrine-containing third layer are produced.

In the tableting step, it is also possible to place the isopropylantipyrine-containing tableting granules first in a die of the tableting machine, precompress them, then add the inactive ingredient granules for tableting, precompress them, and finally add the ibuprofen-containing tableting granules and subject the whole die contents to compression proper.

The dry coated tablets of this invention are characterized by internally having an ibuprofen- or isopropylantipyrine-containing core tablet.

The dry coated tablets of this invention are produced in the following manner.

First, following addition of the above-mentioned excipient, binder, disintegrator, lubricant and so on to ibuprofen, core tablets are produced by tableting in the conventional manner.

These core tablets are preferably subjected to surface coating with a coating agent such as hydroxypropylmethylcellulose, hydroxymethylcellulose, hydroxypropylcellulose or the like.

Separately, isopropylantipyrine-containing tableting granules are produced as mentioned above. The dry coated tablets are produced by placing a portion of the isopropylantipyrine-containing tableting granules in a die of the tableting machine, placing thereon one of the above-mentioned ibuprofen-containing core tablets and further placing thereon the isopropylantipyrine-containing tableting granules, followed by compressing.

It is also possible to prepare core tablets from isopropylantipyrine and cause ibuprofen-containing tableting granules to surround each core tablet, to produce dry coated tablets. The core tablets preferably contain the smaller in quantity of the two ingredients ibuprofen and isopropylantipyrine.

The contents of ibuprofen and isopropylantipyrine in each three-layer tablet or dry coated tablet are respectively within the range of 10 mg to 150 mg, preferably 25 mg to 150 mg, and the weight ratio therebetween is preferably 5:1 to 1:5, more preferably 3:1 to 1:3, as mentioned hereinbefore.

In the production of such solid preparations as hard capsules, powders, granules and fine granules, mere blending of IBP and IPA tends to result in melting due to melting point depression.

Therefore, these solid preparations are preferably produced, like the three-layer tablets mentioned above, by separately preparing ibuprofen-containing granules and isopropylantipyrine-containing granules, coating one or both of the granule species with a coating agent such as hydroxypropylmethyicellulose, and then blending both the granule species.

Each preparation thus produced is orally administered to patients one to three times a day.

The following test examples illustrate the effects of the mixture composition of this invention.

Test Example 1

Pain Removing Effect

Test substances and doses:

IPA and IBP were respectively suspended in a 0.5% aqueous solution of methylcellulose (MC) to a concentration of 8 mg/ml. The test suspensions for groups 2 and 3 were prepared by mixing the IPA suspension and IBP suspension together in a proportion of 3:1 (group 2) or 1:3 (group 3). The doses used are shown below. Each suspension was orally administered at a volumetric dose of 5 ml/kg.

Group 1: IPA 40 mg/kg+IBP 0 mg/kg
Group 2: IPA 30 mg/kg+IBP 10 mg/kg
Group 3: IPA 10 mg/kg+IBP 30 mg/kg
Group 4: IPA 0 mg/kg +IBP 40 mg/kg Test method:

Six-week-old male SD strain rats (Nippon SLC) fasted 24 hours before experiment were used in groups of 10. They were grouped such that the four groups were uniform in mean body weight.

According to the Randall-Selitto method, the right hind paw of each animal was given an increasing pressure stimulus using an Analgesy meter (Ugo Basile), and the weight under which the animal first showed an avoidance response was measured as a pain threshold. First, the pain threshold value before thermal stimulation was measured (0 hour value). Then, heat edema was caused on the right hind leg of the rat by immersing said leg in hot water (54° C.) just to the fibular ankle (boundary showing sudden change in hair density) for 12 seconds. Two hours later, the pain threshold of the right hind leg was measured (2 hours value), immediately followed by test substance administration. After the lapse of two further hours, the pain threshold of the right hind leg was measured (4 hours value).

The percent pain removal was calculated by the following formula:

$$\text{Pain removal} = \frac{\text{4 hours value} - \text{2 hours value}}{\text{0 hour value} - \text{2 hours value}} \times 100(\%)$$

The results thus obtained are shown in Table 1.

TABLE 1

| Dose (mg/kg PO) | | |
|---|---|---|
| IPA | IBP | Pain removal (%) |
| 40 | 0 | 25.8 ± 15.9 |
| 30 | 10 | 49.0 ± 8.7 |
| 10 | 30 | 55.4 ± 8.6 |
| 0 | 40 | 32.3 ± 7.5 |

(Mean ± standard error)

As is evident from Table 1, the combined administration of IPA and IBP in weight ratios of 3:1 and 1:3 with the total dose being maintained constant resulted in superior pain removing effects as compared with the single administration of IPA or IBP.

The mixture composition of this invention is therefore useful as an antipyretic analgesic agent. Furthermore, a total dose of IBP and IPA which is smaller than the effective dose of IBP or IPA used singly can produce substantially the same degree of analgesic effect as said effective dose of IBP or IPA, hence the manifestation of their adverse effects is expected to be reduced accordingly.

Test Example 2

Dissolution Test

Test preparation:
A: Three-layer tablets of Example 3 mentioned later herein;
B: Tablets of Reference Example 1 mentioned later herein.

Test method:
Japanese Pharmacopeia, 12th edition, Dissolution test II (paddle method)
(First solution, 900 ml, 37 C., 100 r.p.m.)
Test Results:

TABLE 2

| | Dissolution of ibuprofen (%) | | | | | | | |
|---|---|---|---|---|---|---|---|---|
| (min) | 5 | 10 | 15 | 20 | 30 | 40 | 50 | 60 |
| A | 29.3 | 46.2 | 55.4 | 61.5 | 69.1 | 74.1 | 77.5 | 80.1 |
| B | 29.9 | 48.0 | 57.6 | 63.9 | 71.8 | 76.9 | 80.6 | 83.4 |

(Mean of 3 measurements)

The results of the dissolution test indicate that the dissolubility of ibuprofen from the test preparation A is good and almost the same as that from B.

Test Example 3

Absorption Test

Six beagle dogs (body weight: about 10 kg) fasted overnight were orally administered with one tablet each of the above-mentioned preparations A and B together with 100 ml of water by the crossover method (2-week interval).

At 0.25, 0.5, 1, 2, 3, 4, 6 and 8 hours after administration, blood samples were collected into heparinized tubes.

After centrifugation, plasma levels of ibuprofen were measured by high-performance liquid chromatography and, further, the Cmax (maximum plasma concentration), Tmax (time required for arriving at maximum plasma concentration) and AUC (area under curve for 8-hour period following administration) values were determined.

Test results:

TABLE 3

| Test preparation | Plasma ibuprofen concentration (μg/ml) | | | | | | | |
|---|---|---|---|---|---|---|---|---|
| | 0.25 hr | 0.5 hr | 1 hr | 2 hr | 3 hr | 4 hr | 6 hr | 8 hr |
| A | 3.93 ±4.13 | 13.24 ±8.38 | 22.60 ±5.89 | 17.49 ±3.23 | 11.94 ±4.14 | 8.15 ±3.11 | 4.38 ±2.40 | 2.41 ±1.57 |
| B | 8.20 ±8.65 | 12.37 ±10.07 | 14.91 ±6.45 | 13.76 ±2.58 | 10.44 ±2.89 | 8.14 ±3.33 | 5.39 ±3.35 | 2.94 ±2.04 |

| Test preparation | Cmax (μg/ml) | Tmax (hr) | AUC 0→8 hr |
|---|---|---|---|
| A | 24.47 ±4.27 | 1.08 ±0.49 | 75.72 ±17.33 |
| B | 17.04 ±5.25 | 1.50 ±1.00 | 68.00 ±23.46 |

(mean of 6 dogs ± standard deviation)

The three-layer tablets (test preparation A) of this invention give a significantly higher Cmax value as compared with the conventional tablets (test preparation B) (analysis of variance, P<0.01).

Therefore, increased ibuprofen absorption can be attained with the three-layer tablets of this invention than with the single active ingredient preparation.

The following examples illustrate this invention in further detail.

Example 1

(1) Ibuprofen, isopropylantipyrine, lactose, low substituted hydroxypropylcellulose and hydroxypropylcellulose were mixed up and the resulting mixture was granulated using a PharmaMatrix granulator (Nara Kikai Seisakusho). The granules were then dried under vacuum at 40° C. and adjusted to an appropriate size using a multiple granule size adjuster (Hata Tekkosho). Magnesium stearate was added to the granules and the whole mixture was tableted using a P-18 tableting machine (Hata Tekkosho) to give uncoated tablets each having the following composition:

| (Uncoated tablet composition) | |
|---|---|
| Ibuprofen | 120 mg |
| Isopropylantipyrine | 40 mg |
| Lactose | 14 mg |
| Low substituted hydroxypropylcellulose | 20 mg |
| Hydroxypropylcellulose | 4 mg |
| Magnesium stearate | 2 mg |
| Total | 200 mg |

(2) The uncoated tablets obtained above in (1) were coated with a coating solution having the composition shown below using a HiCoater HCT-55 coater (Freund Sangyo) under the conditions of feed air temperature of 55° C. and exhaust gas temperature of 40° C. to give film-coated tablets.

| (Coating solution composition) | |
|---|---|
| Hydroxypropylcellulose | 5.9 mg |
| Yellow iron sesquioxide | 0.1 mg |
| (Distilled water) | (100 μl) |
| Total | 6 mg |

Example 2

Uncoated tablets each having the composition shown below were obtained by proceeding in the same manner as in Example 1-(1).

| Ibuprofen | 40 mg |
|---|---|
| Isopropylantipyrine | 120 mg |
| Lactose | 14 mg |
| Low substituted hydroxypropylcellulose | 20 mg |
| Hydroxypropylcellulose | 4 mg |
| Magnesium stearate | 2 mg |
| Total | 200 mg |

Example 3

(1) Ibuprofen, anhydrous caffeine, lactose, crosscarmellose sodium and hydroxypropylmethylcellulose were mixed up, purified water was added to the mixture, and the whole mixture was granulated and dried in the conventional manner.

To the granules obtained were added crystalline cellulose, light anhydrous silicic acid, magnesium stearate and talc, followed by mixing up to give ibuprofen-containing tableting granules for forming the first layer of a three-layer tablet, with the following composition:

| (First layer composition) | |
|---|---|
| Ibuprofen | 50 mg |
| Anhydrous caffeine | 50 mg |
| Lactose | 48 mg |
| Crosscarmellose sodium | 20 mg |
| Hydroxypropylmethylcellulose | 4 mg |
| Crystalline cellulose | 20 mg |
| Light anhydrous silicic acid | 2 mg |
| Magnesium stearate | 1 mg |
| Talc | 5 mg |
| Total | 200 mg |

(2) Lactose, crystalline cellulose and magnesium stearate were mixed up and processed to give tableting granules composed of the inactive ingredients alone and intended for forming the second layer of the three-layer tablet, with the following composition:

| (Second layer composition) | |
|---|---|
| Lactose | 44.85 mg |
| Crystalline cellulose | 5 mg |
| Magnesium stearate | 0.15 mg |
| Total | 50 mg |

(3) Isopropylantipyrine-containing tableting granules for forming the third layer of the three-layer tablet were obtained by proceeding in the same manner as in Example 3-(1), with the following composition:

| (Third layer composition) | |
|---|---|
| Isopropylantipyrine | 150 mg |
| Crosscarmellose sodium | 20 mg |
| Hydroxypropylmethylcellulose | 4 mg |
| Crystalline cellulose | 18 mg |
| Light anhydrous silicic acid | 2 mg |
| Magnesium stearate | 1 mg |
| Talc | 5 mg |
| Total | 200 mg |

(4) The ibuprofen-containing tableting granules obtained above in (1) (200 mg) were placed in a mortar of a tableting machine and lightly precompressed. Then, the mortar was shifted on the turntable, and 50 mg of the tableting granules composed of inactive ingredients as obtained above in (2) were placed in the mortar, followed by light precompressing. Finally, the mortar was shifted on the turntable, 200 mg of the isopropylantipyrine-containing tableting granules obtained above in (3) were placed in the mortar, and the whole mortar contents were subjected to compression proper to give a three-layer tablet having a total weight of 450 mg.

Reference Example 1

The ibuprofen-containing tableting granules obtained in Example 3-(1) were tableted on a tableting machine to give ibuprofen tablets each containing 50 mg of ibuprofen.

Example 4

(1) Ibuprofen, lactose, crosscarmellose sodium and hydroxypropylcellulose were mixed up, purified water was added to the mixture, and the whole mixture was granulated and dried in the conventional manner.

To the granules were added crystalline cellulose, light anhydrous silicic acid, magnesium stearate and talc, followed by mixing up and tableting in the conventional manner.

The thus-obtained tablets were then coated with a coating solution prepared by dissolving hydroxypropylmethylcellulose in purified water, to give core tablets each having the following composition:

| (Core tablet composition) | |
|---|---|
| Ibuprofen | 50 mg |
| Lactose | 30 mg |
| Crosscarmellose sodium | 10 mg |
| Hydroxypropylcellulose | 2.5 mg |
| Crystalline cellulose | 10 mg |
| Light anhydrous silicic acid | 1 mg |
| Magnesium stearate | 0.5 mg |
| Talc | 3 mg |
| Hydroxypropylmethylcellulose | 3 mg |
| Total | 110 mg |

(2) Isopropylantipyrine-containing tableting granules were obtained by proceeding in the same manner as in Example 3-(1).

| (Tableting granule composition) | |
|---|---|
| Isopropylantipyrine | 150 mg |
| Anhydrous caffeine | 50 mg |
| Crosscarmellose sodium | 32 mg |
| Hydroxypropylmethylcellulose | 6.5 mg |
| Crystalline cellulose | 29 mg |
| Light anhydrous silicic acid | 3 mg |
| Magnesium stearate | 1.5 mg |
| Talc | 8 mg |
| Total | 280 mg |

(3) The isopropylantipyrine-containing tableting granules obtained in Example 4-(2) (140 mg) were placed in a mortar of a tableting machine, the ibuprofen-containing core tablet obtained in Example 4-(1) was placed thereon, and 140 mg of the isopropylantipyrine-containing tableting granules obtained in Example 4-(2) were placed further thereon. The whole mortar contents were subjected to compression proper to give a dry coated tablet with a total weight of 390 mg.

Example 5

(1) Granules were produced by mixing up isopropylantipyrine, anhydrous caffeine, lactose, crosscarmellose sodium and hydroxypropylcellulose, adding purified water thereto, granulating the resultant mixture and drying the granules in the conventional manner.

The granules were coated with a coating solution prepared by dissolving hydroxypropylmethylcellulose in purified water to give isopropylantipyrine-containing granules.

| Isopropylantipyrine | 50 weight parts |
|---|---|
| Anhydrous caffeine | 50 weight parts |
| Lactose | 48 weight parts |
| Crosscarmellose sodium | 20 weight parts |
| Hydroxypropylcellulose | 4 weight parts |
| Hydroxypropylmethylcellulose | 3 weight parts |

(2) Ibuprofen-containing granules (uncoated) having the composition shown below were produced in the same manner as in Example 5-(1). The granules were mixed with the isopropylantipyrine-containing granules of Example 5-(1) to give a granular composition.

| Ibuprofen | 150 weight parts |
|---|---|
| Crosscarmellose sodium | 20 weight parts |
| Hydroxypropylcellulose | 4 weight parts |

Example 6

Ibuprofen (5 g) and isopropylantipyrine (15 g) were added to purified water (400 ml), and the mixture was stirred. After further addition of sucrose (300 g), D-sorbitol (200 g), saccharin sodium (3 g), sodium citrate (3 g), sodium benzoate (2 g) and a strawberry flavor (1 ml), the whole mixture was stirred and diluted with purified water to a total volume of 1 liter. A suspension syrup was thus obtained.

What is claimed is:

1. A pharmaceutical composition, which comprises an analgesically and/or antipyretically effective amount of each of ibuprofen and isopropylantipyrine.

2. The pharmaceutical composition of claim 1, wherein a proportion of ibuprofen to isopropylantipyrine of about 5:1 to 1:5 by weight is used.

3. The pharmaceutical composition of claim 2, wherein the proportion of ibuprofen to isopropylantipyrine of about 3:1 to 1:3 by weight is used.

4. The pharmaceutical composition of claim 1, wherein said composition has a dosage form of a 3-layer tablet, comprising an ibuprofen-containing first layer, an isopropylantipyrine-containing third layer, and a second layer therebetween composed of one or more inactive ingredients.

5. The pharmaceutical composition of claim 1, wherein said composition has a dosage form of a dry coated tablet.

6. The pharmaceutical composition of claim 4, wherein said composition has a dosage form of a dry coated tablet.

7. The pharmaceutical composition of claim 1, which further contains excipients, binders, disintegrators, lubricants, anhydrous caffeine, bromovalerylurea, allylisopropylacetylurea, bromodiethylacetylurea, butylisopropylurea, or ephedrine.

8. The pharmaceutical composition of claim 4, which further comprises excipients, binders, disintegrators, lubricants, anhydrous caffeine, bromovalerylurea, allylisopropylacetylurea, bromodiethylacetylurea, butylisopropylurea, or ephedrine.

9. The pharmaceutical composition of claim 5, wherein said dry coated tablet is coated with a coating agent selected from the group consisting of hydroxypropylmethylcellulose, hydroxymethylcellulose and hydroxypropylcellulose.

10. The pharmaceutical composition of claim 6, wherein said dry coated tablet is coated with a coating agent selected from the group consisting of hydroxypropylmethylcellulose, hydroxymethylcellulose and hydroxypropylcellulose.

* * * * *